US00PP15448P2

(12) United States Plant Patent
Pierce

(10) Patent No.: US PP15,448 P2
(45) Date of Patent: Dec. 21, 2004

(54) ***CALIBRACHOA* PLANT NAMED 'CAL LITELAVER'**

(50) Latin Name: ***Calibrachoa* sp.**
Varietal Denomination: Cal Litelaver

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,366

(22) Filed: Apr. 5, 2004

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of *Calibrachoa* plant named 'Cal Litelaver', characterized by its uniform, outwardly spreading, mounding and trailing plant habit; freely and continuous branching habit; dense and bushy plant growth habit; and very freely flowering habit, numerous light lavender-colored flowers with yellow-colored throats.

1 Drawing Sheet

Botanical classification/cultivar designation: *Calibrachoa sp.* cultivar Cal Litelaver.

BACKGROUND OF THE INVENTION

The present Invention relates to a new and distinct cultivar of *Calibrachoa* plant, botanically known as *Calibrachoa sp.,* and hereinafter referred to by the cultivar name 'Cal Litlaver'.

The new *Calibrachoa* is a product of a planned breeding program conducted by the Inventor in Gilroy, Calif. The objective of the breeding program is to create new *Calibrachoas* with uniform plant growth habit and flowering and flowers that remain open.

The new *Calibrachoa* originated from a cross-pollination made by the Inventor in September, 2000 of a proprietary *Calibrachoa* selection identified as 38-1, not patented, as the female, or seed parent, with a proprietary *Calibrachoa* selection identified as 77-4, not patented, as the male, or pollen parent. The new *Calibrachoa* was selected as a single flowering plant from the resulting progeny by the Inventor in a controlled environment in April, 2001 in Gilroy, Calif.

Asexual reproduction of the new cultivar by terminal cuttings taken in Gilroy, Calif. since April, 2001 has shown that the unique features of this new *Calibrachoa* are stable and reproduced true to type in successive generations.

SUMMARY OF THE INVENTION

Plants of the cultivar Cal Litlaver have not been observed under all possible environmental conditions. The phenotype may vary somewhat with variations in environment such as temperature and light intensity without, however, any variance in genotype.

The following traits have been repeatedly observed and are determined to be the unique characteristics of 'Cal Litlaver'. These characteristics in combination distinguish 'Cal Litlaver' as a new and distinct cultivar:

1. Uniform, outwardly spreading, mounding and trailing plant habit.
2. Freely and continuous branching habit; dense and bushy plant growth habit.

3. Very freely flowering habit, numerous light lavender-colored flowers with yellow-colored throats.

In side-by-side comparisons conducted in Gilroy, Calif., plants of the new *Calibrachoa* differed from plants of the female parent selection in the following characteristics:

1. Plants of the new *Calibrachoa* were more freely basally branching than plants of the female parent selection.
2. Plants of the new *Calibrachoa* had smaller leaves than plants of the female parent selection.
3. Plants of the new *Calibrachoa* and the female parent selection differed in flower coloration as plants of the female parent selection had pink-colored flowers.

In side-by-side comparisons conducted in Gilroy, Calif., plants of the new *Calibrachoa* differed from plants of the male parent selection in the following characteristics:

1. Plants of the new *Calibrachoa* were more freely basally branching than plants of the male parent selection.
2. Plants of the new *Calibrachoa* had darker green-colored leaves than plants of the male parent selection.
3. Plants of the new *Calibrachoa* flowered earlier than plants of the male parent selection.
4. Plants of the new *Calibrachoa* and the male parent selection differed in flower coloration as plants of the male parent selection had magenta pink-colored flowers.

Plants of the new *Calibrachoa* can be compared to plants of the *Calibrachoa* cultivar Million Bells Sweet Pink, not patented. In side-by-side comparisons conducted in Gilroy, Calif., plants of the new *Calibrachoa* differed from plants of the cultivar Million Bells Sweet Pink in the following characteristics:

1. Plants of the new *Calibrachoa* were more upright than plants of the cultivar Million Bells Sweet Pink.
2. Plants of the new *Calibrachoa* had longer internodes than plants of the cultivar Million Bells Sweet Pink.
3. Plants of the new *Calibrachoa* had lighter lavender-colored flowers whereas plants of the cultivar Million Bells Sweet Pink had red purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Cal Litelaver' grown in a container.

The photograph at the bottom of the sheet comprises a close-up view of typical flowers and leaves of 'Cal Litelaver'.

DETAILED BOTANICAL DESCRIPTION

The aforementioned photographs and following observations and measurements describe plants grown in Gilroy, Calif., under commercial practice during the summer in a polycarbonate-covered greenhouse with day temperatures about 24 to 34° C., night temperatures about 13 to 18° C., and light levels about 2,000 foot-candles. One rooted cutting was planted per 15.25-cm container. Plants were pinched one time and were grown for about 12 weeks. In the following description, color references are made to The Royal Horticultural Society Colour Chart, 1995 Edition, except where general terms of ordinary dictionary significance are used.

Botanical classification: *Calibrachoa* sp. cultivar Cal Litelaver.

Parentage:

*Female parent.*—Proprietary *Calibrachoa* sp. selection identified as 38-1, not patented.

*Male parent.*—Proprietary *Calibrachoa* sp. selection identified as 77-4, not patented.

Propagation:

*Type cutting.*—Terminal vegetative cuttings.

*Time to initiate roots, summer and winter.*—About 7 to 10 days at 22° C.

*Time to develop roots.*—About three to four weeks at 22° C.

*Root description.*—Fibrous; white in color.

*Rooting habit.*—Freely branching.

Plant description:

*Form.*—Annual flowering plant; uniform, low mounding, outwardly spreading and trailing plant habit; plants eventually becoming hemispherical to spherical in shape. Freely and continuously branching habit with about ten main lateral branches per plant with lateral branches forming potentially at every node; dense and bushy plant growth habit. Vigorous growth habit.

*Usage.*—Appropriate for hanging baskets, window boxes, patio containers and landscape applications.

*Plant height.*—About 21 cm.

*Plant diameter.*—About 62 cm.

*Lateral branches.*—Length: About 34 cm. Diameter: About 3 mm. Internode length: About 2.2 cm. Texture: Pubescent; slightly coarse. Color: 144A.

*Foliage description.*—Arrangement: Alternate, simple. Length: About 4.3 cm. Width: About 1.6 cm. Shape: Obovate. Apex: Rounded to broadly acute. Base: Attenuate. Margin: Entire. Texture, upper and lower surfaces: Slightly pubescent along margins; very slightly glandular. Venation pattern: Pinnate, arcuate. Color: Developing foliage, upper surface: 146A. Developing foliage, lower surface: 146B. Fully expanded foliage, upper surface: 147A. Fully expanded foliage, lower surface: 147B. Venation, upper surface: 147B. Venation, lower surface: 147C. Petiole length: About 1 cm. Petiole diameter: About 2 mm. Petiole color: 147B.

Flower description:

*Flower type and habit.*—Salverform flowers; single, axillary. Flowers face mostly upward or outward and are held above and beyond the foliage. Flowers persistent.

*Quantity of flowers.*—Very freely flowering, typically about 400 open flowers and flower buds per plant.

*Natural flowering season.*—Long day responsive; spring until frost in the autumn; flowering continuous during the flowering period.

*Flower longevity on the plant.*—About one week.

*Fragrance.*—None detected.

*Flower diameter.*—About 2.7 cm.

*Flower depth (height).*—About 1.7 cm.

*Flower throat diameter.*—About 6 mm.

*Flower buds (showing color).*—Length: About 1.8 cm. Diameter: About 4 mm. Shape: Elongated oblong. Color: 75D.

*Corolla.*—Arrangement/appearance: Single whorl of five petals, fused into flared trumpet with distinct clefts between petal lobes. Petal length from throat: About 1.2 cm. Petal width: About 1.2 cm. Petal shape: Spatulate, fan-shaped to obovate. Petal apex: Rounded. Petal margin: Entire. Petal texture, upper and lower surfaces: Smooth, velvety. Color: Petal, upper surface, when opening: 80A; towards the throat, 67A. Petal, lower surface, when opening: 75B. Petal, upper surface, fully opened: 80C; towards the throat, 80A; color becoming closer to 77C to 77D with development. Petal, lower surface, fully opened: 78D. Flower throat (inside): 5A. Flower tube (outside): 78D. Venation, upper and lower petal surfaces: Same as petal color. Venation, throat and tube: Same as throat and tube colors.

*Sepals.*—Arrangement/appearance: Single whorl of five petals fused at base, star-shaped. Length: About 1 cm. Width: About 2.5 mm. Shape: Narrowly lanceolate. Apex: Broadly acute. Margin: Entire. Texture, upper and lower surfaces: Pubescent. Color, immature and mature, upper surface: 147A. Color, immature and mature, lower surface: 147B.

*Peduncles.*—Length: About 2.7 cm. Width: About 1 mm. Angle: About 45 to 60° to the stem. Strength: Strong. Texture: Pubescent. Color: 144A.

*Reproductive organs.*—Stamens: Quantity/arrangement: Five. Anther shape: Ovoid. Anther length: Less than 1 mm. Anther color: 8A. Pollen amount: Scarce. Pollen color: 7A. Pistils: Quantity: One. Pistil length: About 9 mm. Stigma shape: Rounded. Stigma color: 145A. Style length: About 6 mm. Style color: 145D. Ovary color: 145A.

*Seed/fruit.*—Seed and fruit production has not been observed.

Disease/pest resistance: Plants of the new *Calibrachoa* have not been noted to be resistant to pathogens or pests common to *Calibrachoa.*

It is claimed:

1. A new and distinct cultivar of *Calibrachoa* plant named 'Cal Litelaver', as illustrated and described.

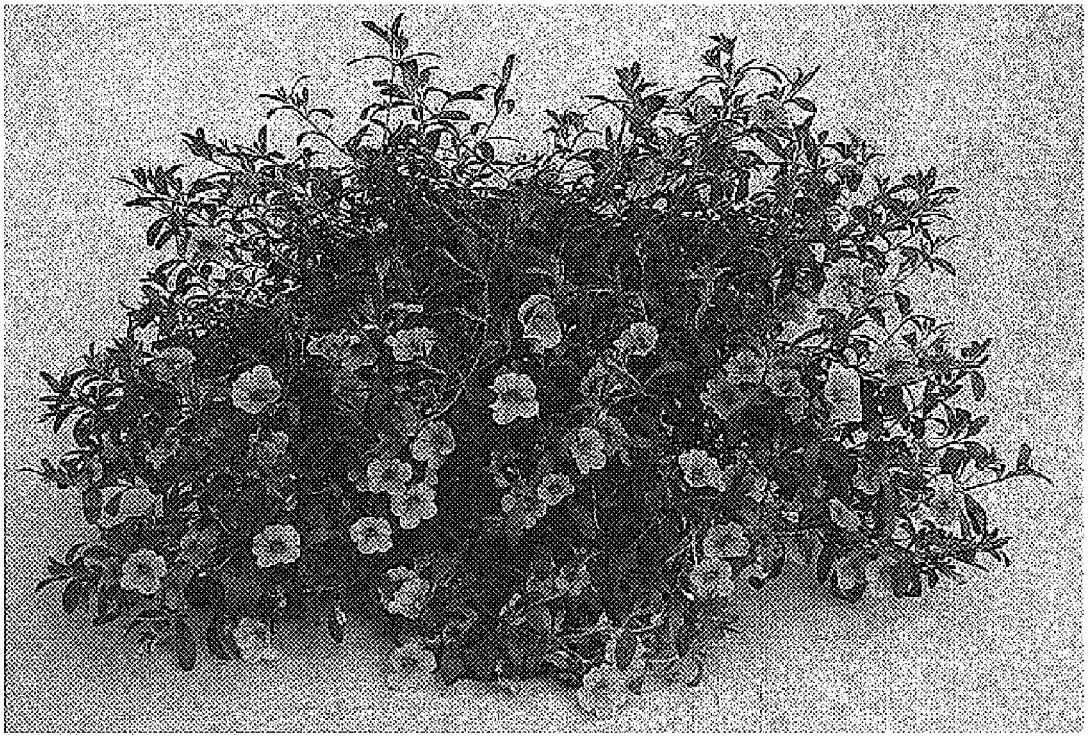
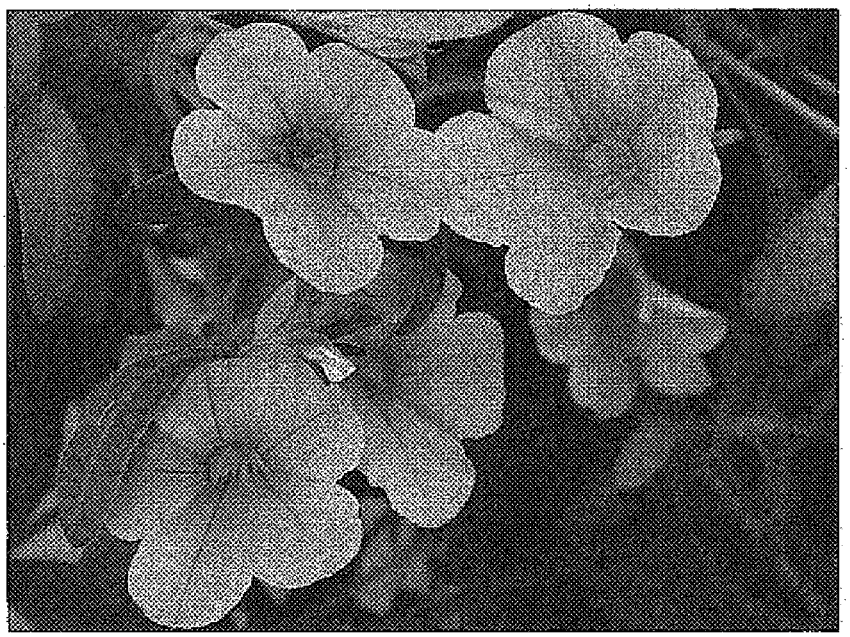

* * * * *